(12) United States Patent
Szybalski et al.

(10) Patent No.: US 6,472,177 B1
(45) Date of Patent: Oct. 29, 2002

(54) EXPRESSION VECTOR WITH DUAL CONTROL OF REPLICATION AND TRANSCRIPTION

(75) Inventors: Waclaw T. Szybalski; Jadwiga Wild; Zdenka Hradecna, all of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/840,783

(22) Filed: Apr. 23, 2001

(51) Int. Cl.$^7$ ............................ C12P 21/02; C12N 1/21; C12N 15/63; C12N 15/70; C12N 15/79

(52) U.S. Cl. .................... 435/69.1; 435/243; 435/320.1

(58) Field of Search ............................ 435/69.1, 320.1, 435/243

(56) References Cited

U.S. PATENT DOCUMENTS 5,874,259 A    2/1999   Szybalski

OTHER PUBLICATIONS

Durland, R.H. et al., "Mutations in the trfA Replication Gene of the Broad–Host–Range Plasmid RK2 Result in Elevated Plasmid Copy Numbers," *Journal of Bacteriology* 172:3859–3867 (1990).
Fang, F.C. et al., "Mutations in the gene encoding and replication–initiation protein of plasmid RK2 produce elevated copy numbers of RK2 derivatives in *Escherichia coli* and distantly related bacteria," *Gene* 133:1–8 (1993).
Hamilton, C.M., "A Binary–BAC system for plant transformation with high–molecular-weight DNA," *Gene* 200:107–116 (1997).
Haugan, K. et al., "The Phenotypes of Temperature–Sensitive Mii–RK2 Replicons Carrying Mutations in the Replication Control Gene trfA Are SuppressedNonspecifically by Intragenic cop Mutations," *Journal of Bacteriology* 174:7026–7032 (1992).
Haugan, K. et al., "The Host Range of RK2 Minimal Replicon Copy–Up Mutants is Limited by Species–Specific Differences in the Maximum Tolerable Copy Number," *Plasmid* 33:27–39 (1995).
Kim, U–J et al., "Construction and Characterization of a Human Bacterial Artificial Chromosome Library," *Genomics* 34:213–218 (1996).
Koob, M. et al., "Cleaving Yeast and *Escherichia coli* Genomes at a Single Site," *Science*, 250:271–273 (1990).
Lutz, R. et al., "Independent and tight regulation of transcriptional units in *Escherichia coli* via the LacR/O, the TetR/O and AraC/$I_1$ –$I_2$ regulatory elements," *Nucl. Acids Res.* 25:1203–1210 (1997).
Posfai, G. et al., "In vivo excision and amplification of large segments of the *Escherichia coli* genome," *Nucleic Acids Research* 22(12): 2392–2398 (1994).
Shizuya, H. et al., "Cloning and stable maintenance of 300–kilobase–pair fragments of human DNA in *Escherichia coli* using and F–factor based vector," *Proc. Natl. Acad. Sci. USA* 89:8794–8797 (1992).
Szybalski, Waclaw, "From the double–helix to novel approaches to the sequencing of large genomes," *Gene* 135:279–290 (1993).
Wild, J. et al., "A broad–host–range in vivo pop–out and amplification system for generating large quantities of 50– to 100–kb genomic fragments for direct DNA sequencing," *Gene* 179:181–188 (1996).

*Primary Examiner*—Terry McKelvey
(74) *Attorney, Agent, or Firm*—Quarles & Brady LLP

(57) ABSTRACT

The present invention provides an expression vector adapted for inducible amplification and inducible transcription of a heterologous polynucleotide operably linked to a transcriptional promoter provided in the vector. The invention further provides a method for using the vector to produce large quantities of a heterologous polypeptide encoded by the heterologous polynucleotide. The pBAC of the present invention is derived from a BAC cloning vector by modifying the BAC cloning vector to include a conditional ori for amplifying the pBAC and an inducible promoter for regulating the transcription of an inserted gene. Both the conditional ori and the inducible promoter can be activated jointly or separately by suitable signals in a host cell. Once a polynucleotide of interest is inserted into the pBAC and the pBAC is introduced into a host cell, the level of the product encoded by the polynucleotide can be controlled by regulating the copy number of the expression vector or the activity of the promoter under which transcription of the inserted polynucleotide is controlled, or both.

76 Claims, 3 Drawing Sheets

HOST: Any ara⁻ E. coli strain

EXPRESSION VECTOR WITH DUAL CONTROL OF REPLICATION AND TRANSCRIPTION

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to processes and expression vectors for producing and recovering heterologous polypeptides from bacterial cells. More particularly, the invention relates to expression vectors that comprise polynucleotide control sequences that permit simultaneous or independent control over both the level at which the polypeptide-encoding polynucleotide sequences are transcribed and the copy number of the expression vectors.

In a typical expression system, heterologous polypeptide production is either not regulated or is regulated by modulating transcription from a transcriptional promoter operably linked upstream of a polynucleotide that encodes the heterologous polypeptide. To ensure that large amounts of protein are produced, expression vectors having high-copy-number are typically employed. In such high-copy-number expression systems, when the promoter that regulates transcription of the polypeptide-encoding sequence is not tightly regulated (is "leaky"), even small amounts of the polypeptide produced can be toxic to, or can have other adverse effects upon, the host cell. Also, high-copy-number expression vectors can be unstable and can yield undesired deletions or mutations or chimeric recombination products. This is a rather common disadvantage of high-copy-number vectors.

Alternatively, a host cell can better tolerate transcriptional leakage when the expression vector is present in one or a few copies per cell. However, such vectors are also of limited utility in that the amount of polypeptide produced from a single-copy vector is very small and large numbers of cells containing such a vector carrying the polynucleotide of interest must be grown to obtain sufficient quantities of the polypeptide for isolation and purification.

Bacterial artificial chromosome (BAC) vectors (and plasmid forms, pBAC) are single-copy vectors used to maintain large genomic DNA fragments, and have not been used as expression vectors. BAC (or pBAC) vectors typically accommodate inserts in the range of up to 300 kilobase pairs. Kim, U-J et al., "Construction and Characterization of a Human Bacterial Artificial Chromosome Library," Genomics 34:213–218 (1996) describe a now widely used BAC cloning vector, pBeloBAC11, that uses lacZ X-Gal/IPTG complementation to distinguish by color insert-containing recombinant molecules from colonies carrying the BAC vector without an insert. The pBeloBAC11, is an improvement over pBAC 108L, a prior BAC cloning vector described in Shizuya, H., "Cloning and stable maintenance of 300-kilobase-pair fragments of human DNA in *Escherichia coli* using an F-factor-based vector," P.N.A.S. U.S.A. 89:8794–8797 (1992) that lacked the ability to identify insert-containing BACs. U.S. Pat. No. 5,874,259 (incorporated herein as if fully set forth in its entirety) discloses conditionally amplifiable BAC vectors having, in addition to an F factor-based origin of replication that maintains the vector at one copy per cell, a conditional origin of replication at which replication is initiated in response to a suitable signal in the host cell. The disclosed vectors facilitate obtaining large amounts of a genomic polynucleotide fragment, thereby overcoming a known disadvantage of BAC vectors, namely low DNA yield. After induction, the copy number of the vector or the insert-containing vector increases substantially and the polynucleotides of interest can be isolated. In the vectors of U.S. Pat. No. 5,874,259, a pair of excision-mediating sites (EMS) can optionally flank the conditional ori and a site into which a cloned genomic polynucleotide fragment can be cloned. In the latter case, the nucleic acid between the EMS can be excised to create a circular plasmid that comprises the genomic fragment insert and which can replicate when the conditional ori is activated by induced Rep protein. None of the aforementioned patent and publications contemplate employing BAC vectors for transcribing polynucleotides and none of the vectors includes all of the elements for doing so. While pBeloBAC11 contains the T7 and SP6 promoters, these are used only as sites to anneal the sequencing primers, not as promoters of transcription.

BRIEF SUMMARY OF THE INVENTION

In a first aspect, the present invention is an expression vector for expressing in compatible host cells a heterologous polypeptide encoded by a heterologous polynucleotide sequence in the vector. The expression vector of the invention comprises both a conditionally amplifiable origin of replication (ori) that functions in the host cells and a tightly regulated inducible transcriptional promoter operably linked to the heterologous polynucleotide sequence. The vector is capable of independent replication in the host cell and therefore also can include polynucleotide sequences that encode any proteins required for plasmid replication, maintenance, and partitioning that are not otherwise provided in the host cells, either in the growth medium, in the host genome or on a separate expression vector.

For convenience, the expression vector also preferably contains a selectable marker for confirming the presence in the host cells of the vector. The vector also preferably includes at least one cloning site into which the heterologous polynucleotide of interest can be cloned. It is also desirable to distinguish clones that contain a heterologous polynucleotide of interest from the expression vector itself. In accord with conventional practice, the cloning site can therefore be situated in a larger polynucleotide coding sequence that confers an alterable phenotype upon the host cells. A change in that phenotype can indicate that a heterologous polynucleotide is present in the cloning site. An expression vector of the invention can optionally include a pair of excision mediation sites (EMS) flanking the conditional ori, the inducible promoter and the site into which the polynucleotide of interest is inserted, for excision of the expression cassette from the vector to a separate, smaller, and conditionally-amplifiable plasmid.

In a related aspect, the invention is also summarized in that a host cell for producing heterologous polypeptides includes in its interior an expression vector of the present invention. The host cell can conditionally provide the signals required to activate the conditional ori and/or the inducible promoter in the modified vector. The expression vector in the host cell can comprise a heterologous polynucleotide insert that encodes the polypeptide of interest.

In yet another related aspect, the invention is further summarized in that a method for obtaining a desired amount of the heterologous polypeptide of interest from a host cell that contains the expression vector with heterologous polynucleotide insert includes the steps of modulating the activity in the host cell of an agent that conditionally amplifies the ori to maintain the vector at a desired copy number and modulating the activity of an agent that induces a desired transcription level of the heterologous polynucleotide to maintain an overall desired level of polypeptide production from the vector, and isolating the heterologous polypeptide from the host cells.

It is an object of the present invention to produce heterologous polypeptides in a host cell, even where the polypeptide is toxic or has other adverse effects on the host cell that would prevent cloning and/or stable maintenance of inserted polynucleotide prior to the overproduction of the polypeptide in conventional cell-based protein expression systems.

It is another object of the present invention to retain the advantageous properties of existing vectors including stability of an inserted polynucleotide.

It is a feature of the present invention that the vector includes both a conditional origin of replication and an inducible transcriptional promoter.

It is a feature of the present invention that the expression vector allows user control over both vector copy number and transcription level.

It is another feature of the present invention that, in the presence of inducing signals, the copy number of the heterologous polynucleotide in the host cells increases from 1 copy to between at least about 10 and 100 copies or higher which can be, but is not limited to and the cellular machinery transcribes the copied polynucleotides.

It is an advantage of the present invention that host cells that comprise a vector of the invention are more tolerant of promoter leakage before induction than cells in conventional systems because the vector is maintained as a single-copy or at very low copy number.

It is a further advantage of the present invention that the host cells are able to produce large quantities of a heterologous polypeptide, even toxic polypeptides, because the cells both amplify the vector and transcribe the polypeptide quickly after induction such that large-scale protein production is complete before the polypeptide can adversely affect the cells. Before induction, a leaky transcriptional promoter can have little effect on the cells, because the vector copy number is so low.

Other objects, advantages, and features of the present invention, including more efficient preparation of the vector for the cloning, and simplified purification of the DNA or protein product, will become apparent upon consideration of the following detailed description taken in conjunction with the accompanying drawings.

DETAILED DESCRIPTION OF THE PREFERRED EMBODIMENT

Figure 1:
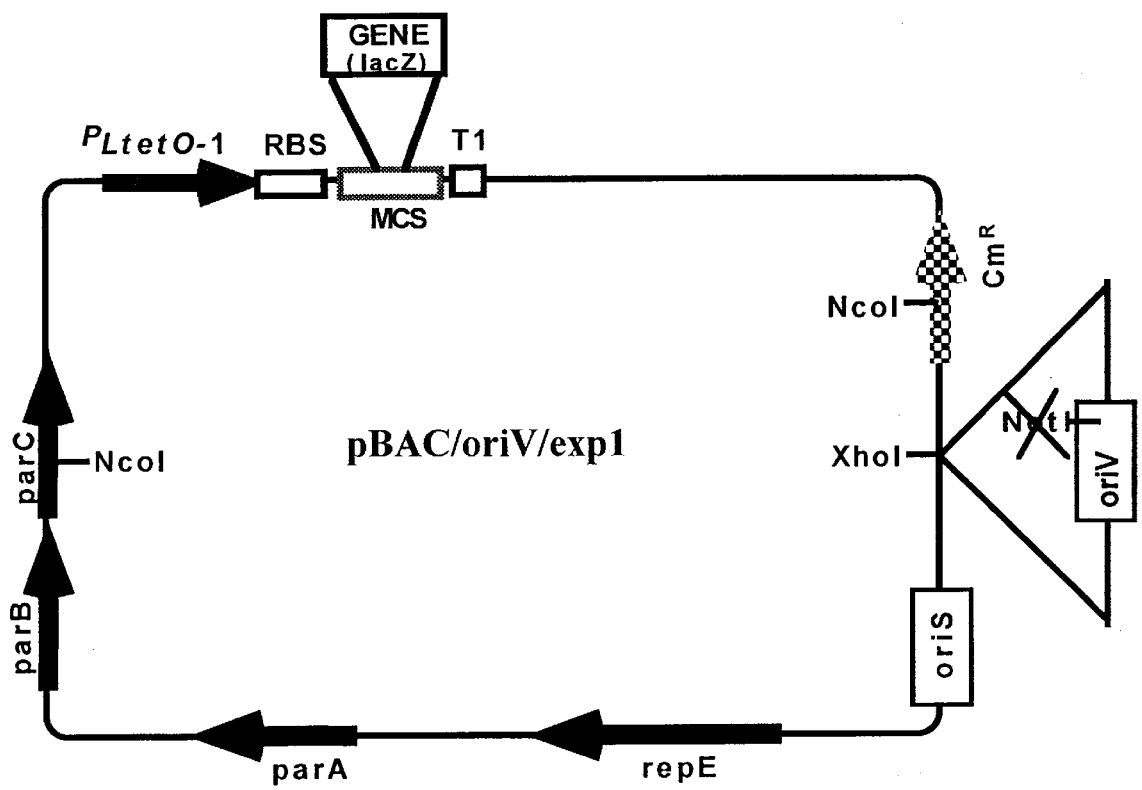
FIGS. 1, 2 and 3 schematically depict vectors prepared in accordance with the present invention.

A preferred expression vector of the invention is a bacterial artificial chromosome (BAC or pBAC), but the principles of the invention can apply with equal force to other polynucleotide expression vectors. A skilled artisan is familiar with the kinds of genetic manipulation used to create new vectors or to modify existing vectors in accord with the invention. To produce a BAC or pBAC vector of the present invention, a conditional origin of replication (ori) for amplifying the vector and an inducible promoter for regulating the transcription of a heterologous polynucleotide insert are provided on the vector. The present invention provides dual control over the expression of heterologous polypeptide in a host cell. One aspect of control lies in the regulation of the promoter activity. The other aspect of control lies in the increase of copy number from one to about 10 to about 100 per cell. Amplification of and transcription from a BAC vector modified as described can be separately or coordinately regulated to control the amount of heterologous polypeptide produced in the host cells. For maximum expression, the promoter is induced to the highest level of activity allowable and the ori is induced to maximize copy number. However, the ability to engage both mechanisms independently makes it possible to achieve a range of polypeptide levels not achievable using either mechanism separately.

The methods for physically modifying the vectors, including but not limited to nucleic acid cleavage, amplification, reverse transcription, ligation, and the like, are well within the level of skill in the art and are not detailed herein. Modifications in accordance with the present invention are described relative to pBeloBAC11, although one skilled in the art can readily make the same changes to other plasmids including, but not limited to, pBAC108L.

Although the invention is described in terms of a modified BAC vector, the skilled artisan will appreciate that other non-BAC cloning vectors can be adapted as described herein. Examples of other suitable single-copy or low-copy cloning vectors that can employ this approach include P1 and pSC101 plasmids. The BAC model is particularly desirable as it has been shown to accommodate very large DNA inserts and keep them without being subject to deletions or other rearrangements. Moreover, pBAC/oriV vectors described in U.S. Pat. No. 5,874,259 are clearly superior since they are not only truly single-copy vectors, but are also very stable and permit easy amplification to high-copy number.

Both the conditional ori and the inducible promoter can be activated by suitable signals in a host cell. The agents can be positive regulators or can interact with negative regulators to increase amplification and transcription as desired. A positive regulator (inducer) acts by providing a signal that increases an activity while a negative regulator (repressor) prevents an activity until an agent (also historically designated as inducer) prevents the negative regulation. The agents can be organic or inorganic chemical agents or can be polypeptides encoded by polynucleotide sequences in the host cell genome or on an extrachromosomal vector present in the host cell. Alternatively, the agents can be administered manually to the host cells by, e.g., providing the agent in the growth medium. Preferably, the inducing agent(s) increase transcription and/or replication to an extent proportional to their level in the host cell. The skilled artisan will appreciate that it is within the level of skill in the art to provide as simple or as complex a regulatory scheme as desired for ensuring that the appropriate agent is available to the vector at the appropriate time. The precise nature of that scheme is not critical to the invention. Rather, for purposes of this invention, it is understood that the ultimate agents for amplifying the vector and for inducing transcription can be provided as needed.

Conditional origins of replication are known to the art and the details of inducible amplification are not repeated herein. Of course, the conditional origin is chosen for compatibility with a known inducing agent provided as disclosed herein, for its normally tight downregulation in the selected host cells in the absence of the compatible inducing agent, and for its strong inducible operability in the presence of the inducing agent. The conditional origin is provided in addition to a origin of replication that maintains the vector at a single copy per cell. One such suitable origin is oriS which maintains the vector at a single copy when glucose is present at about 0.2% in the growth medium.

The conditional ori, when provided in combination with the compatible inducing agent, should have sufficient activity to amplify the vector to a copy number sufficient to produce an adequate amount of the heterologous polypeptide after inducing transcription. It is also preferred that such origin of replication have a broad host range to accommodate shuttling the vector among different cell types. A preferred conditional ori is oriV, GenBank No. L 13843, although the conditional ori could be any ori that functions in the host cell and is normally inactive until exposed to the replication-inducing agent.

It is preferred but not essential that replication be conditioned upon the presence of a single agent, such as a protein, although multi-agent replication systems are known. If the inducing agent is encoded by polynucleotide, the sequence that encodes the polynucleotide can be provided in an expression cassette under the transcriptional control of an inducible promoter, which can be the same or different from the inducible promoter that controls the transcription of the heterologous polynucleotide. Similarly, the replication-inducing agent can be induced by the same agent that induces transcription from the transcriptional promoter. The expression cassette can be provided in the host cell genome, on the vector itself or on another polynucleotide element such as a low-, medium-, or high-copy number plasmid that contains an origin of replication. The skilled artisan will thus appreciate that the dual aspects of vector control can be coordinately or separately regulated. Either way, after replication is induced by the agent, replication begins and the vector copy number increases. The oriV is preferred because it has a broad host range, it can replicate DNA fragments of even 100-kb or larger, it can amplify to high-copy-number and it requires only one inducing protein (TrfA or a copy-up mutant thereof), the structure of which is known to the art. The copy number of the vector can be controlled by the mutant TrfA protein that retains an ability to induce DNA replication, such mutants being known to the art, which in turn is controlled by the promoter activity level. In the presence of mutant TrfA, a vector that comprises oriV is induced to replicate to high-copy-number, such as more than at least about 10 copies per cell, preferably more than about 50 copies per cell, and still more preferably at least about 80 to 100 copies per cell, or more. When the oriV/TrfA system is used, the vector is suited for use in any Gram-negative oriV/TrfA compatible host. Other known conditional origins of replication that can be used in the invention include but are not limited to pBBR1 and RSF1010.

Inducible promoters are known to the art and a detailed summary of the state of the art is not provided herein. A suitable inducible promoter functions in the selected host cell and responds to an inducing agent with sufficient strength to promote a high level of transcription of a downstream heterologous polynucleotide operably linked to the inducible transcriptional promoter in the vector. In this application, "operably linked" means that the promoter is situated upstream of the polynucleotide coding sequence such that productive transcription of the polynucleotide is initiated at the promoter. "Heterologous" refers to a polynucleotide or polypeptide not natively found in or produced by the host cells. The term "polypeptide" broadly encompasses all proteinaceous molecules including, without limitation, oligopeptides, peptides and proteins, as those terms are understood in the art. A high level of transcription yields ample amounts of protein, at least about 1%, preferably between 1% and 10% of cell weight, but can be higher. Before induction, in contrast, the promoter should normally be inactive, resulting in insignificant or undetectable levels of product as measured by conventional detection methods in the non-induced state. It is also preferred that the promoter require only a single agent for induction. Although the inducible promoter could be any promoter having these attributes, preferred inducible promoters are the araC/$P_{araBAD}$ (activator gene)-promoter (araC-$P_{araBAD}$; GenBank Accession No. X 81838 nt 1–1277) and the TetR/$P_{LtetO}$ repressor promoter ($P_{LetO}$; GenBank Accession No. U 66312). These promoters are preferable because they are tightly regulated when non-induced, and very strong when induced. These two promoters can be activated by treating the host cells with 0.01% L-arabinose ( LA) and 100 ng/ml anhydrotetracycline (aTc), Lutz et al., 25 *N.A.R.* 1203 (1997), respectively. Concentrations of LA and aTc shown above are believed optimal but are not essential. AraC/$P_{araBAD}$ also responds to an anti-inducer, D-fucose. Thus, the activity of AraC/$P_{araBAD}$ can be regulated by adjusting the LA/D-fucose ratio. Other suitable inducible promoters include, but are not limited to, $P_{tac}$, $P_{tac}$, T5, T7, and others.

In a method for conditionally producing a heterologous polypeptide, vectors thus modified can be inserted into suitable host cells using standard nucleic acid transfer methods such as electroporation, calcium-mediated transformation or cos-mediated phage lambda packaging and transfection. A suitable host cell includes facility for conditional expression of the agents that can modulate amplification of the vector and transcription from the transcriptional promoter. The host cell strain is preferably bacterial, preferably an *E. coli* strain, but can be a plant, yeast, or animal cell, including a mammalian cell, as long as the conditional ori and the inducible promoter in the BAC vector, as well as the activating functions, are selected so as to function in the selected host. One could also employ shuttle vectors incorporating the critical single-copy and amplification elements of pBAC/oriV, or also regular BAC. Hamilton, C. M., "A Binary-BAC system for plant transformation with high-molecular weight DNA," *Gene* 200:107–116 (1997) describes a BAC shuttle vector for use also in plant cells, but without the disclosed amplification feature.

The present invention will be better understood upon consideration of the following non-limiting example.

EXAMPLES

A BAC expression vector of the present invention was obtained by modifying existing pBeloBAC11 (Kim, U-J, et al., supra; GenBank Accession Number U51113) for on demand amplification of the vector. The oriV element of broad host-range plasmid RK2 was inserted at the unique XhoI site of pBeloBAC11 to create pBAC/oriV. Procedures for preparing such plasmids and for delivering the plasmids into host cells are described in U.S. Pat. No. 5,874,259, and are similar to those in Wild, J. et al., *Gene* 179:181–188 (1997), particularly the references cited in the legend accompanying FIG. 4 thereof, all of which are incorporated herein by reference. The modified vector, depicted schematically in FIG. 1, can receive a heterologous polynucleotide in its own MCS in the manner analogous as pBeloBAC 11 receives genomic DNA fragments.

To provide the TrfA replicator protein, gene trfA, carrying various copy-up mutations that retain the ability to act as a replicator protein (see U.S. Pat. No. 5,874,259) was placed under the transcriptional control of either the AraC/$P_{araBAD}$ activator/promoter or the TetR/$P_{LtetO}$ repressor promoter. These trfA cassettes were placed either on the host genome (using att/Int system) or cloned into the unique SalI site on the pBAC/oriV vector. In the Example, the functionality of the copy-number control aspect of the invention was demonstrated by showing that the vector copy number increases when it comprises oriV. The ability to function as an expression vector was demonstrated by transcribing trfA from the vector in the presence of an inducing agent. The subsequently translated trfA protein induced replication from oriV.

In the first embodiment (FIG. 1), the pBAC/oriV plasmid contains the $P_{LtetO}$ promoter cloned in the SalI site with the lacZ reporter gene in an MCS downstream of the promoter. The host cells used were the *E. coli* strain DH10b re-engineered to contain the $P_{araBAD}$-trfA203 operon in the host chromosomal lacZ gene and to constitutively express the tetR gene inserted at host attB site. In this case, the reporter lacZ gene expression is regulated by aTc and the plasmid amplification by L-arabinose.

Figure 2:
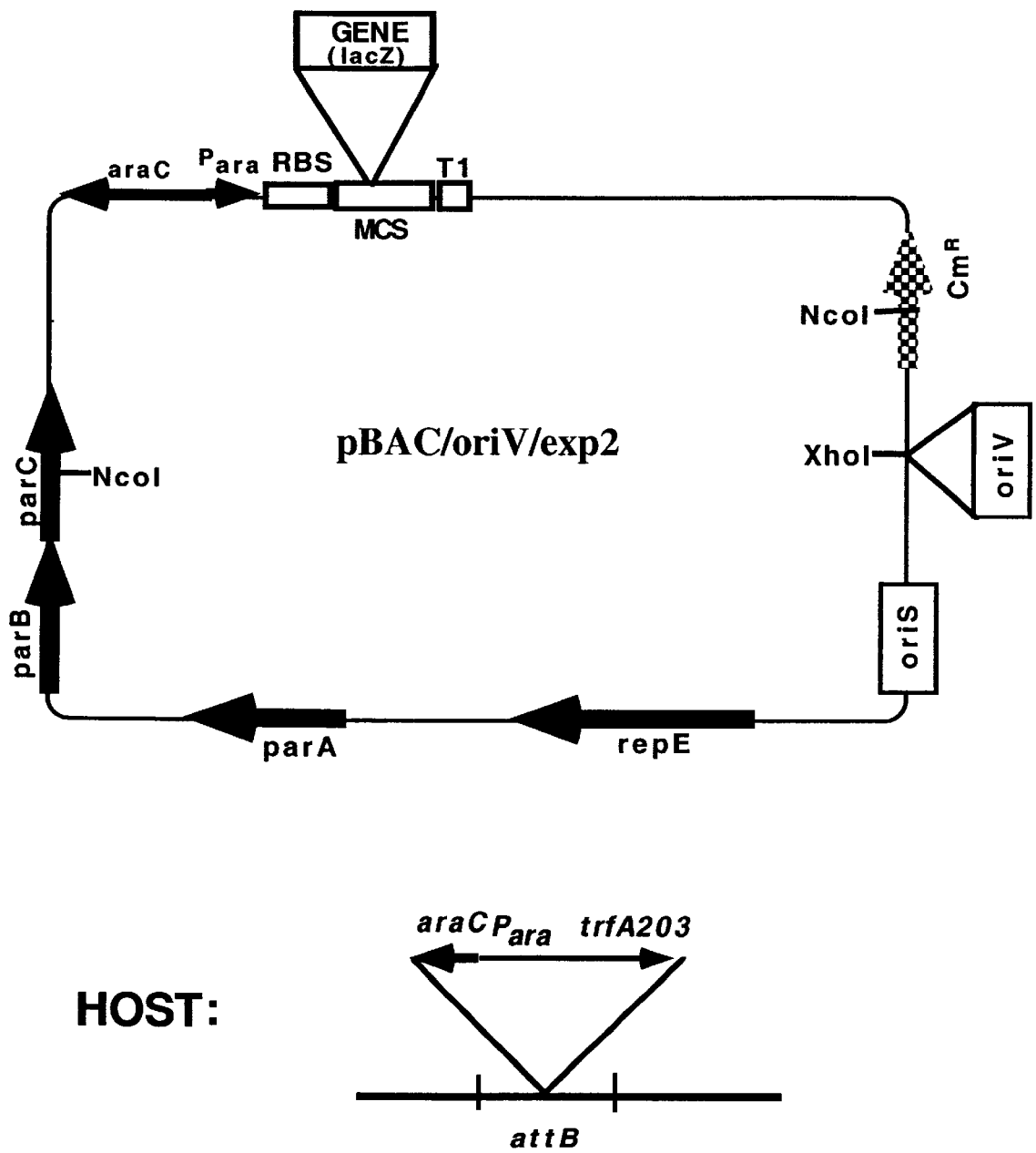

In the second embodiment (FIG. 2), the pBAC/oriV plasmid contains the $P_{araBAD}$ promoter cloned in the SalI site with the lacZ reporter gene in a multi-cloning site (MCS) downstream of the promoter. The host cells used were E. coli strain DH10b re-engineered to contain the $P_{araBAD}$-trfA203 operon in the host attB site. In this case, both the reporter lacZ expression and the plasmid amplification are regulated by L-arabinose.

Figure 3:
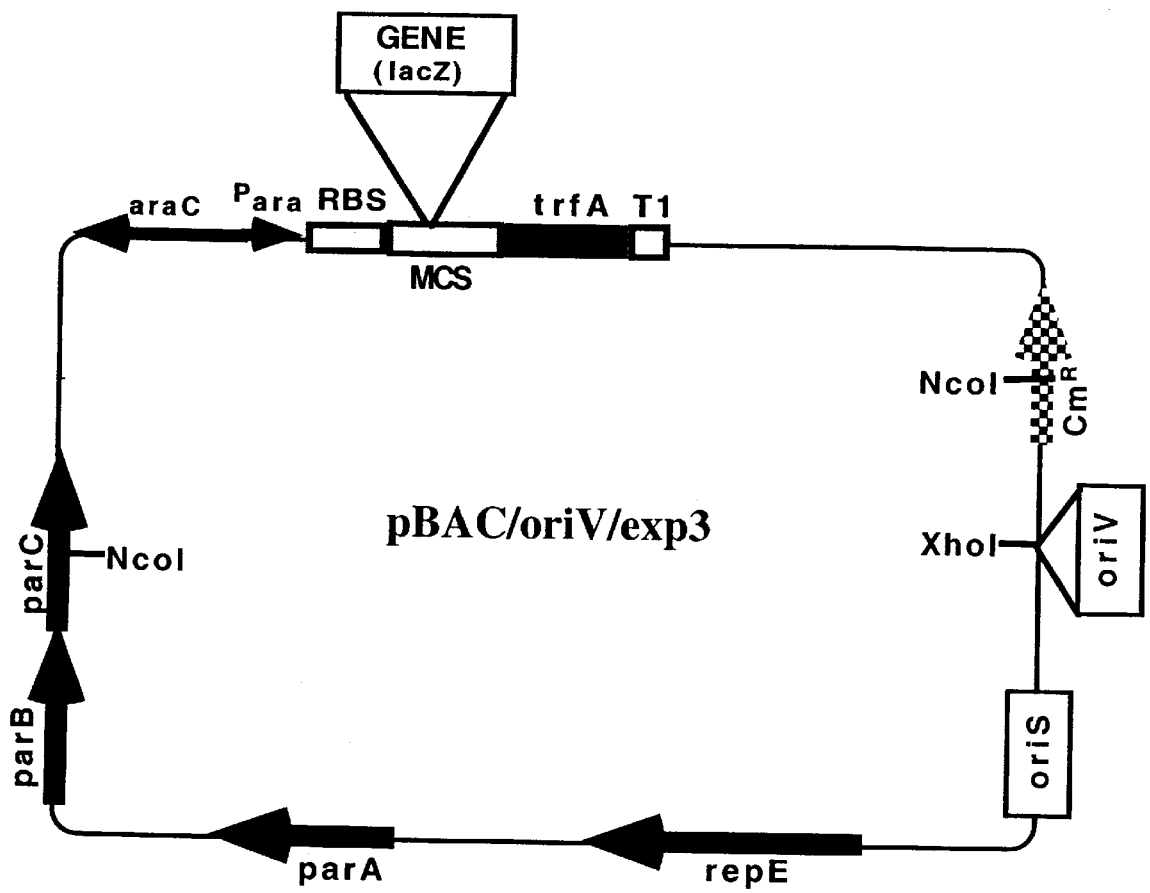

In the third embodiment (FIG. 3), the pBAC/oriV plasmid contains the $P_{araBAD}$-trfA203 operon cloned in the SalI site, with the lacZ reporter gene in an MCS downstream of the $P_{araBAD}$-trfA203 operon. The host cells used any *E. coli* strains, preferably electrocompetent and of the DH10b type. In this case, both the reporter lacZ expression and the plasmid amplification are regulated by L-arabinose.

In these strains we measured the lacZ expression in the Miller's units and found it to be negligible in the absence of L-arabinose inducer (embodiments 2 and 3) or in the absence of L-arabinose and aTc inducers (embodiment 1). In the presence of 0.2% glucose, trfA was completely repressed and the vector remained at 1copy/cell. Upon induction, with 0.01% L-arabinose or 100 ng/ml aTc there was high amplification of the pBAC/oriV clones to about 100 copies/cell. Massive amounts (over 30,000 Miller's units) of the lacZ product (beta-galactosidase) were produced; the protein product was isolated on the gel or by any other procedure.

The present invention is not intended to be limited to the foregoing but rather to encompass all such variations and modifications as come within the scope of the appended claims.

We claim:

1. An expression vector for transcribing in a host cell a heterologous polynucleotide that encodes a heterologous polypeptide, the expression vector comprising:
   a conditional origin of replication responsive to a replication-inducing agent; and
   a first transcriptional promoter responsive to a transcription-inducing agent and operably linked upstream of the heterologous polynucleotide,
   wherein the encoded polypeptide is toxic to the host cell.

2. The expression vector of claim 1, wherein the transcriptional promoter is $P_{araBAD}$.

3. The expression vector of claim 2 wherein the transcription-inducing agent is L-arabinose.

4. The expression vector of claim 1, wherein the transcriptional promoter is $P_{LtetO}$.

5. The expression vector of claim 4, wherein the transcription-inducing agent is anhydrotetracycline.

6. The expression vector of claim 1, wherein the conditional origin of replication is oriV.

7. The expression vector of claim 6, wherein the replication-inducing agent is selected from the group consisting of TrfA and a mutant thereof that encodes a replication-inducing agent.

8. The expression vector of claim 1, further comprising a polynucleotide that encodes a replication-inducing agent and a second transcriptional promoter responsive to a transcription-inducing agent operably linked upstream of said polynucleotide.

9. The expression vector of claim 8, wherein the second transcriptional promoter is $P_{araBAD}$.

10. The expression vector of claim 9 wherein the transcription-inducing agent is L-arabinose.

11. The expression vector of claim 8, wherein the second transcriptional promoter is $P_{LtetO}$.

12. The expression vector of claim 11, wherein the transcription-inducing agent is anhydrotetracycline.

13. The expression vector of claim 8, wherein the origin of replication is oriV and the replication inducing agent is selected from the group consisting of TfrA and a mutant thereof that encodes a replication-inducing agent.

14. The expression vector of claim 1, wherein the replication-inducing agent is encoded by the heterologous polynucleotide.

15. The expression vector of claim 14, wherein the transcriptional promoter is $P_{araBAD}$.

16. The expression vector of claim 14 wherein the transcription-inducing agent is L-arabinose.

17. The expression vector of claim 14, wherein the transcriptional promoter is $P_{LtetO}$.

18. The expression vector of claim 17, wherein the transcription-inducing agent is anhydrotetracycline.

19. The expression vector of claim 1, wherein the vector comprises a bacterial artificial chromosome.

20. A bacterial artificial chromosome for transcribing in a host cell a heterologous polynucleotide that encodes a heterologous polypeptide, the bacterial artificial chromosome, comprising:
   a conditional origin of replication responsive to a replication-inducing agent; and
   a transcriptional promoter responsive to a transcription-inducing agent operably linked upstream of the heterologous polynucleotide,
   wherein the encoded polypeptide is toxic to the host cell and the transcriptional promoter is selected from the group consisting of $P_{araBAD}$ and $P_{LtetO}$ and the conditional origin of replication is oriV.

21. A bacterial artificial chromosome as claimed in claim 20 wherein the transcription promoter is $P_{araBAD}$ and the transcription-inducting agent is L-arabinose.

22. A bacterial artificial chromosome as claimed in claim 20 wherein the transcription promoter is $P_{LtetO}$ and the transcription-inducting agent is anhydrotetracycline.

23. A host cell, comprising in its interior:
   an expression vector that comprises an origin of replication responsive to a replication-inducing agent, the expression vector further comprising a transcriptional promoter responsive to a transcription-inducing agent and operably linked upstream of a heterologous polynucleotide that encodes a heterologous polypeptide, wherein the encoded polypeptide is toxic to the host cell.

24. The host cell of claim 23 wherein the vector further comprises a polynucleotide that encodes a replication-inducing agent operably linked to an upstream transcriptional promoter responsive to a transcription-inducing agent.

25. The host cell of claim 24 wherein the polynucleotide that encodes the replication-inducing agent and the operably linked upstream transcription promoter are not encoded on the expression vector.

26. The host cell of claim 25, wherein the transcriptional promoter operably linked to the replication-inducing agent is $P_{araBAD}$.

27. The host cell of claim 26 wherein the transcription-inducing agent is L-arabinose.

28. The host cell of claim 25, wherein the transcriptional promoter operably linked to the replication-inducing agent is $P_{LtetO}$.

29. The host cell of claim 28, wherein the transcription-inducing agent is anhydrotetracycline.

30. The host cell of claim 23, wherein the origin of replication is oriV and the replication-inducing agent is selected from the group consisting of TfrA and a mutant thereof that encodes a replication-inducing agent.

31. A method for inducing expression of a heterologous polypeptide in a host cell that comprises an expression vector, the expression vector comprising an origin of replication responsive to a replication-inducing agent and a transcriptional promoter responsive to a transcription-inducing agent and operably linked upstream of a heterologous polynucleotide that encodes the heterologous polypeptide, the heterologous polypeptide being toxic to the host cell, the method comprising the steps of:

inducing replication of the expression vector; and inducing transcription from the transcriptional promoter operably linked to the heterologous polynucleotide.

32. The method of claim 31 wherein the step of inducing replication comprises the step of inducing transcription in the host cell of a polynucleotide that encodes the replication-inducing agent.

33. The method of claim 31 wherein the step of inducing transcription comprises the step of exposing the host cell to a transcription-inducing agent.

34. The method of claim 31 wherein the replication-inducing step and the transcription-inducing step are coordinately regulated.

35. The method of claim 33 wherein the step of exposing the host cell to a transcription-inducing agent induces transcription of a polynucleotide that encodes the replication-inducing agent.

36. An expression vector for transcribing a heterologous polynucleotide that encodes a heterologous polypeptide, the expression vector comprising:

a conditional origin of replication responsive to a replication-inducing agent;

a first transcriptional promoter responsive to a transcription-inducing agent and operably linked upstream of the heterologous polynucleotide; and a second transcriptional promoter responsive to the transcription-inducing agent and operably linked upstream of a polynucleotide that encodes the replication-inducing agent, wherein the heterologous polynucleotide is transcribed and the vector replicates in the presence of the transcription-inducing agent.

37. An expression vector as claimed in claim 36 wherein the first and second transcriptional promoters are identical.

38. The expression vector of claim 36, wherein at least one transcriptional promoter is $P_{araBAD}$.

39. The expression vector of claim 38 wherein the transcription-inducing agent is L-arabinose.

40. The expression vector of claim 36, wherein at least one transcriptional promoter is $P_{LtetO}$.

41. The expression vector of claim 40, wherein the transcription-inducing agent is anhydrotetracycline.

42. The expression vector of claim 36, wherein the conditional origin of replication is oriV.

43. The expression vector of claim 42, wherein the replication-inducing agent is selected from the group consisting of TrfA and a mutant thereof that encodes a replication-inducing agent.

44. A bacterial artificial chromosome for transcribing a heterologous polynucleotide that encodes a heterologous polypeptide, the bacterial artificial chromosome, comprising:

a conditional origin of replication responsive to a replication-inducing agent;

a first transcriptional promoter responsive to a transcription-inducing agent and operably linked upstream of the heterologous polynucleotide; and a second transcriptional promoter responsive to the transcription-inducing agent and operably linked upstream of a polynucleotide that encodes the replication-inducing agent, wherein the heterologous polynucleotide is transcribed and the vector replicates in the presence of the transcription-inducing agent.

45. A bacterial artificial chromosome as claimed in claim 44, wherein at least one transcriptional promoter is selected from the group consisting of $P_{araBAD}$ and $P_{LtetO}$ and the conditional origin of replication is oriV.

46. A bacterial artificial chromosome as claimed in claim 45 wherein the transcription promoter is $P_{araBAD}$ and the transcription-inducing agent is L-arabinose.

47. A bacterial artificial chromosome as claimed in claim 45 wherein the transcription promoter is $P_{LtetO}$ and the transcription-inducing agent is anhydrotetracycline.

48. A host cell, comprising in its interior the expression vector of claim 36.

49. The host cell of claim 48 wherein the first and second transcriptional promoters are identical.

50. The host cell of claim 48, wherein at least one transcriptional promoter is $P_{araBAD}$.

51. The host cell of claim 50 wherein the transcription-inducing agent is L-arabinose.

52. The host cell of claim 48, wherein at least one transcriptional promoter is $P_{LtetO}$.

53. The host cell of claim 52, wherein the transcription-inducing agent is anhydrotetracycline.

54. The host cell of claim 48, wherein the conditional origin of replication is oriV.

55. The host cell of claim 54, wherein the replication-inducing agent is selected from the group consisting of TrfA and a mutant thereof that encodes a replication-inducing agent.

56. A method for inducing expression of a heterologous polypeptide in a host cell that comprises the expression vector of claim 36, the method comprising the steps of:

inducing transcription of the heterologous polynucleotide; and inducing transcription of the polynucleotide that encodes the replication-inducing agent.

57. The method of claim 56 wherein the replication-inducing step and the transcription-inducing step are coordinately regulated.

58. The method of claim 57 wherein the step of inducing transcription of the heterologous polynucleotide induces transcription of the polynucleotide that encodes the replication-inducing agent.

59. An expression vector for transcribing a heterologous polynucleotide that encodes a heterologous polypeptide, the expression vector comprising:

a conditional origin of replication responsive to a replication-inducing agent; and a transcriptional promoter responsive to a transcription-inducing agent and operably linked upstream of the heterologous polynucleotide and upstream of a polynucleotide that encodes the replication-inducing agent, wherein the heterologous polynucleotide is transcribed and the vector replicates in the presence of the transcription-inducing agent.

60. The expression vector of claim 59, wherein the transcriptional promoter is $P_{araBAD}$.

61. The expression vector of claim 60 wherein the transcription-inducing agent is L-arabinose.

62. The expression vector of claim 59, wherein the transcriptional promoter is $P_{LtetO}$.

63. The expression vector of claim 62, wherein the transcription-inducing agent is anhydrotetracycline.

64. The expression vector of claim 59, wherein the origin of replication is oriV.

65. The expression vector of claim 59, wherein the replication inducing agent is selected from the group consisting of TfrA and a mutant thereof that encodes a replication-inducing agent.

66. A bacterial artificial chromosome for transcribing a heterologous polynucleotide that encodes a heterologous polypeptide, the bacterial artificial chromosome, comprising:

a conditional origin of replication responsive to a replication-inducing agent; and a transcriptional promoter responsive to a transcription-inducing agent and operably linked upstream of the heterologous polynucleotide and upstream of a polynucleotide that encodes the replication-inducing agent, wherein the heterologous polynucleotide is transcribed and the vector replicates in the presence of the transcription-inducing agent.

67. A bacterial artificial chromosome as claimed in claim 66, wherein the transcriptional promoter is selected from the group consisting of $P_{araBAD}$ and $P_{LtetO}$ and the conditional origin of replication is oriV.

68. A bacterial artificial chromosome as claimed in claim 67 wherein the transcriptional promoter is $P_{araBAD}$ and the transcription-inducing agent is L-arabinose.

69. A bacterial artificial chromosome as claimed in claim 67 wherein the transcriptional promoter is $P_{LtetO}$ and the transcription-inducing agent is anhydrotetracycline.

70. A host cell, comprising in its interior the expression vector of claim 59.

71. The host cell of claim 70, wherein the transcriptional promoter is $P_{araBAD}$.

72. The host cell of claim 71 wherein the transcription-inducing agent is L-arabinose.

73. The host cell of claim 70, wherein the transcriptional promoter is $P_{LtetO}$.

74. The host cell of claim 73, wherein the transcription-inducing agent is anhydrotetracycline.

75. The host cell of claim 70, wherein the origin of replication is oriV and the replication-inducing agent is selected from the group consisting of TfrA and a mutant thereof that encodes a replication-inducing agent.

76. A method for inducing expression of a heterologous polypeptide in a host cell that comprises the expression vector of claim 59, the method comprising the step of:

inducing transcription from the transcriptional promoter.

* * * * *